United States Patent [19]

Knutson, Jr.

[11] 4,146,705
[45] Mar. 27, 1979

[54] METHOD FOR INCREASING SOLUTION VISCOSITY OF *ARTHROBACTER STABILIS* POLYSACCHARIDES

[75] Inventor: Clarence A. Knutson, Jr., Peoria, Ill.

[73] Assignee: The United States of America as represented by the Secretary of Agriculture, Washington, D.C.

[21] Appl. No.: 807,620

[22] Filed: Jun. 17, 1977

[51] Int. Cl.$^2$ .............................................. C07H 1/08
[52] U.S. Cl. ...................................... 536/1; 106/208; 252/316; 252/352; 536/115
[58] Field of Search .................................... 536/1, 114

[56] References Cited

U.S. PATENT DOCUMENTS

| | | | |
|---|---|---|---|
| 3,000,790 | 9/1961 | Jeanes et al. | 536/1 |
| 3,054,689 | 9/1962 | Jeanes et al. | 536/1 |
| 3,314,801 | 4/1967 | Cadmus et al. | 536/1 |
| 3,632,570 | 1/1972 | Gill | 536/1 |
| 3,697,498 | 10/1972 | Browning et al. | 536/114 |
| 3,822,250 | 7/1974 | Kimura et al. | 536/1 |
| 3,900,462 | 8/1975 | Komatani et al. | 536/1 |

*Primary Examiner*—Johnnie R. Brown
*Attorney, Agent, or Firm*—M. Howard Silverstein; David G. McConnell; Curtis P. Ribando

[57] ABSTRACT

The extracellular heteropolysaccharide produced by the bacterium *Arthrobacter stabilis* NRRL B-3225 is treated by acidification, drying, and controlled heating to substantially increase its viscosity in aqueous solutions and to tailor it to particular conditions of use.

10 Claims, No Drawings

METHOD FOR INCREASING SOLUTION VISCOSITY OF *ARTHROBACTER STABILIS* POLYSACCHARIDES

BACKGROUND OF THE INVENTION

1. Field of the Invention

This invention relates to a process for treating the extracellular heteropolysaccharide produced by the bacterium *Arthrobacter stabilis* so as to increase its viscosity in aqueous solutions.

2. Description of the Prior Art

Isolation of the *A. stabilis* organism from garden soil, its characterization, and culturing procedures for polysaccharide production are taught by Gill in U.S. Pat. No. 3,632,570, herein incorporated by reference.

The polysaccharide has several potential uses including that of a thickening and suspending agent in aqueous solutions. It is compatible with various solutes, e.g., salts, acids, and cations, and is even characterized by large increases in viscosity in their presence. However, inherent low viscosity (about 300 cps. at 0.5% concentration) of the highly purified native form limits the usefulness of the polysaccharide.

SUMMARY OF THE INVENTION

I have found a process by which the viscosity of aqueous solutions of the extracellular heteropolysaccharide produced by the bacterium *Arthrobacter stabilis* NRRL B-3225 can be increased by as much as 350% or more over that observed by Gill, supra. The increase is permanent, stable, and irreversible and its amount can be controlled by variation of the conditions which produce it. This control permits a wide range of viscosities, thereby enabling aqueous solutions to be tailored to their specific intended uses.

The method of the invention comprises the following steps:

a. providing the *A. stabilis* polysaccharide in its acidified form;
b. drying the acidified polysaccharide from step (a) to below about 25% moisture, dry weight basis; and
c. heating the dried polysaccharide from step (b) to a temperature in the range of from 80° C. to 100° C. for a period of about 130 to about 5 minutes.

The result of increased solution viscosity was totally unexpected, since the normal effect of heating either neutral or acidic polysaccharides in the dry state is to degrade them and cause loss of viscosity. Moreover, U.S. Pat. No. 3,632,570, supra, teaches that, unless salt is present, heating the *A. stabilis* polysaccharide in aqueous solution results in a 33% viscosity loss.

DETAILED DESCRIPTION OF THE INVENTION

The polysaccharide for use in the instant invention is the heteropolysaccharide produced by the bacterium *Arthrobacter stabilis* NRRL B-3225. This microorganism is deposited in the Northern Regional Research Center of the Agricultural Research Service, USDA, in Peoria, Ill. Procedures and conditions for culturing *A. stabilis* are taught in U.S. Pat. No. 3,632,570, though it is understood that the polysaccharide may be obtained from *A. stabilis* cultured by substantially equivalent procedures. Recent comprehensive analysis indicates that the polysaccharide contains D-glucose, D-galactose, pyruvic acid, O-succinyl linked as the half ester, and O-acetyl in an approximate molar ratio of 6:3:1:1:1.5. When purified by the procedure described in Example 1 below and dissolved in water at a 1% level, it imparts a viscosity of about 300 centipoises (cps.). The polysaccharide is recovered from the culture medium by any known procedure including those taught in U.S. Pat. No. 3,632,570. If recovered as a neutral salt, it must subsequently be converted to its acid form by acidification of its pyruvate and succinyl substituent groups. Alternatively, partial or complete acid conversion may be incidental to the recovery procedure, as in the acid dissociation of microbial polysaccharide-polyethoxylated quaternary ammonium compound complexes. For complete conversion, acid may be added directly to a solution of the polysaccharide until the pH is adjusted to within the range of about 1.5 to 2. Suitable acids include strong inorganic and organic acids, such as hydrochloric, sulfuric, phosphoric, chloroacetic, and the like. However, acidification is most easily effected by passage through a cation exchange column.

The acidified polysaccharide is then dried by any conventional means as known in the art to a tack-free condition. Drying to a moisture content of less than about 25%, dry weight basis, is generally acceptable, though for purposes of handling, it is preferred that the moisture content be in the range of about 10-15%, dry weight basis.

Finally, the dried polysaccharide is modified by heating to a temperature in the range of about 80°-100° C. for an inversely related time period ranging from about 130 to about 5 minutes. The rate and degree of modification and the resultant viscosity potential are a function of the conditions of heating. At the preferred temperature of 90° C., the rate is sufficiently moderate to permit full control over the degree of modification. At this temperature, the polysaccharide viscosity potential gradually increases with time until a maximum is reached after about 45 minutes. Beyond this point, the material becomes insoluble with a resultant loss of viscosity potential. Generally, the preferred reaction time ranges from about 40-50 minutes.

After heating, the modified polysaccharide is dissolved in water and neutralized with base. It is not actually certain that the polysaccharide is in solution in the technical sense, and reference to such throughout the disclosure is intended to be inclusive of dispersions as well. Concentrations in the range of 0.2-1% impart sufficient viscosities for most normal uses, though it is understood that concentrations outside of this range could also be used.

The instant method does not adversely affect the polysaccharide's compatibility and viscostability in the presence of salts, acids, cations, and other solutes. As with the native form, the modified polysaccharides yield substantially higher viscosities in the presence of additional solutes such as NaCl and KCl. This property provides another mechanism for tailoring the thickness of solutions. As shown in the accompanying table, viscosities as high as 9600 cps. have been measured for 1% modified polysaccharide solutions in the presence of 0.5% KCl. The preferred concentration of solutes would normally be in the range of about 0.1-3%.

In another embodiment of the invention, the viscosity increase can be varied by converting the polysaccharide only partially to its acidic form prior to drying and heating. For example, a 0.5% solution of a 75% acidified material has a measured viscosity of 1500 cps., whereas a 50% acidified material has a viscosity of 500 cps. Below 50% acidification, the viscosity increase rapidly drops to a negligible level, and it is therefore necessary that the polysaccharide be at least 40% acidified. To this end, it can either be directly converted to the desired acid level or else completely acidified by one of the procedures described above and then backtitrated with base.

The following examples are intended only to further illustrate the invention and are not intended to limit the scope of the invention which is defined by the claims.

EXAMPLE 1

Production of Polysaccharide

Composition of production medium, in grams per 100 ml., was: glucose, 5; tryptone, 0.2; peptone, 0.2; $K_2HPO_4$, 0.5; R salts, 0.5. The initial unadjusted pH was 7.0. Five-hundred milliliter portions were sterilized in Fernbach flasks and inoculated with 30 ml. of vigorously growing culture of *A. stabilis* NRRL B-3225. Flasks were shaken at 25° on a reciprocal shaker 48 hours followed by 48 hours on a rotary shaker. The smooth, mucoid culture had a viscosity of 3080 cps. Culture was made to 35% in ethanol and 1% in chloroform to kill the cells, diluted to a viscosity of 100 cps., and centrifuged in a Sharples continuous supercentrifuge. Bowl residue, consisting of killed cells, was discarded, supernate was made 1% in KCl, and polysaccharide was precipitated by addition of 1 volume of ethanol. The fibrous precipitate was collected by centrifugation, redissolved, diluted to a viscosity of 50 cps., centrifuged twice more, then twice reprecipitated. The purified precipitate was redissolved and dialyzed against distilled water until salt-free. pH of dialyzed sample was 6.1. Sample was filtered through sintered glass, concentrated, and lyophilized. Lyophilized polysaccharide was bottled and stored at 4° C.

Controls A–F

For comparative purposes, controls A–F were prepared by dissolving in water the lyophilized polysaccharide prepared in Example 1 and KCl at the concentrations shown in the table, below. The viscosity of each sample was measured with a Wells-Brookfield RVT cone-plate microviscometer at a standard shear rate of 3.84 sec.$^{-1}$.

EXAMPLES 2–18

A. Treatment of Polysaccharide 0.5-g. Samples of the lyophilized polysaccharide prepared in Example 1 were each dissolved in 500 ml. of water and passed over a column containing 17 ml. of Ag 50 X-4 resin in the hydrogen phase to convert the polysaccharide to its acid form. Each solution in a 1-liter round-bottom flask was then evaporated to dryness under vacuum in a rotary evaporator at a temperature of 30°–32° C. This resulted in a film of polysaccharide being deposited on the inner surface of the flask. The flask was stoppered and immersed in an acid bath preheated to 90° C. for the desired period of time as shown in the table. Each sample was cooled, redissolved in 200 ml. water, and neutralized to pH 6.8 with 0.1N KOH. Approximately 5 ml. KOH were required. The samples were lyophilized to dryness and stored at 4° C. until used.

B. Viscosity Measurement

Examples 2–18 were prepared by dissolving in water the lyophilized polysaccharide prepared in step (A) above and KCl at the concentrations shown in the table, below. The viscosity of each sample was measured with a Wells-Brookfield RVT cone-plate microviscometer at a standard shear rate of 3.84 sec.$^{-1}$.

It is to be understood that the foregoing detailed description is given merely by way of illustration and that modification and variations may be made therein without departing from the spirit and scope of the invention.

Table

| Example | Time heated at 90° C. | Polysacc. conc. | KCl conc. | Viscosity |
| --- | --- | --- | --- | --- |
| A | 0 | 0.5 | 0 | 204.8 |
| B | 0 | 0.5 | 0.5 | 1504.0 |
| C | 0 | 0.5 | 1.0 | 1587.2 |
| D | 0 | 1.0 | 0 | 467.2 |
| E | 0 | 1.0 | 0.5 | 5177.6 |
| F | 0 | 1.0 | 1.0 | 5574.4 |
| 2 | 15 | 0.5 | 0 | 569.6 |
| 3 | 15 | 0.5 | 0.5 | 1689.6 |
| 4 | 15 | 0.5 | 1.0 | 1792.0 |
| 5 | 15 | 1.0 | 0 | 1664.0 |
| 6 | 15 | 1.0 | 0.5 | 6528 |
| 7 | 40 | 0.5 | 0 | 1482.0 |
| 8 | 40 | 0.5 | 0.5 | 2528.0 |
| 9 | 40 | 0.5 | 1.0 | 2444.8 |
| 10 | 40 | 1.0 | 0 | 3718.0 |
| 11 | 40 | 1.0 | 0.5 | 9620.0 |
| 12 | 40 | 1.0 | 1.0 | 9568.0 |
| 13 | 50 | 0.5 | 0 | 1792.0 |
| 14 | 50 | 0.5 | 0.5 | 1145.6 |
| 15 | 50 | 0.5 | 1.0 | 998.4 |
| 16 | 50 | 1.0 | 0 | 4602.0 |
| 17 | 50 | 1.0 | 0.5 | 6110.0 |
| 18 | 50 | 1.0 | 1.0 | 5850.0 |

I claim:

1. A method for treating the extracellular heteropolysaccharide produced by the bacterium *Arthrobacter stabilis* NRRL B-3225 comprising the following steps:
   a. providing said polysaccharide in its acidified form;
   b. drying the acidified polysaccharide from step (a) to below about 25% moisture, dry weight basis; and
   c. heating the dried polysaccharide from step (b) to a temperature in the range of from 80° C. to 100° C. for a time period of from about 130 to about 5 minutes.

2. The method as described in claim 1 wherein said polysaccharide in step (a) is at least 40% acidified.

3. The method as described in claim 1 wherein said polysaccharide in step (a) is completely acidified.

4. The method as described in claim 1 wherein said temperature is about 90° C. and said time period is in the range of about 40–50 minutes.

5. A method for preparing viscous aqueous solutions of the extracellular heteropolysaccharide produced by the bacterium *Arthrobacter stabilis* NRRL B3225 comprising the following steps:
   a. providing said polysaccharide in its acidified form;
   b. drying the acidified polysaccharide from step (a) to below about 25% moisture, dry weight basis;
   c. heating the dried polysaccharide from step (b) to a temperature in the range of from 80° C. to 100° C. for a time period of from about 130 to about 5 minutes;
   d. dissolving said heated polysaccharide from step (c) in water; and
   e. neutralizing said dissolved polysaccharide with base.

6. The method as described in claim 5 wherein said polysaccharide in step (a) is at least 40% acidified.

7. The method as described in claim 5 wherein said polysaccharide in step (a) is completely acidified.

8. The method as described in claim 5 wherein said temperature is about 90° C. and said time period is in the range of about 40–50 minutes.

9. The method as described in claim 5, wherein in step (d) said heated polysaccharide is dissolved in water at a concentration in the range of 0.2–1%.

10. The method as described in claim 5 wherein in step (d) said water contains 0.1–3% of a solute other than said polysaccharide.

* * * * *